United States Patent
Key

(10) Patent No.: US 12,011,489 B2
(45) Date of Patent: Jun. 18, 2024

(54) COMPOSITIONS AND METHODS FOR TREATING INFLAMMATORY DISEASE

(71) Applicant: Christopher Key, Orange, CA (US)

(72) Inventor: Christopher Key, Orange, CA (US)

(73) Assignee: Christopher Key, Orange, CA (US)

( * ) Notice: Subject to any disclaimer, the term of this patent is extended or adjusted under 35 U.S.C. 154(b) by 183 days.

(21) Appl. No.: 17/708,911

(22) Filed: Mar. 30, 2022

(65) Prior Publication Data

US 2023/0310658 A1  Oct. 5, 2023

(51) Int. Cl.
| | |
|---|---|
| *A61K 48/00* | (2006.01) |
| *A61K 35/76* | (2015.01) |
| *A61K 35/761* | (2015.01) |
| *A61K 38/00* | (2006.01) |
| *A61K 38/17* | (2006.01) |

(52) U.S. Cl.
CPC .......... *A61K 48/0066* (2013.01); *A61K 35/76* (2013.01); *A61K 35/761* (2013.01); *A61K 38/177* (2013.01)

(58) Field of Classification Search
CPC .......................... A61K 48/0066; A61K 35/761
See application file for complete search history.

(56) References Cited

U.S. PATENT DOCUMENTS

| | | |
|---|---|---|
| 9,782,453 B2 | 10/2017 | Nicolas |
| 2016/0200765 A1 | 7/2016 | Ganz et al. |
| 2021/0214456 A1 | 7/2021 | Rauner |

FOREIGN PATENT DOCUMENTS

| | | | | |
|---|---|---|---|---|
| WO | WO-0027874 A2 | * | 5/2000 | .............. A61P 25/00 |
| WO | 2014145561 A2 | | 9/2014 | |
| WO | 2020037150 A2 | | 2/2020 | |

OTHER PUBLICATIONS

Kallunki et al. How to Choose the Right Inducible Gene Expression System for Mammalian Studies? Cells 8: 1-16. (Year: 2019).*
Banchini et al. Differential Redox State and Iron Regulation in Chronic Obstructive Pulmonary Disease, Acute Respiratory Distress Syndrome and Coronavirus Disease 2019. Acta Biomed 91: 1-8. (Year: 2020).*
Duca et al. Iron overload and Hepcidin overexpression could play a key role in COVID infection, and may explain vulnerability in elderly, diabetics, and obese patients. Antioxidants 10: 1-12. (Year: 2021).*
Asci et al. Trasferrin receptor 2 gene regulation by microRNA 221 in SH-SY5Ycells treated with MPP+ as Parkinson's disease cellular model. Neuroscience Research 77: 121-127. (Year: 2013).*
Biovian (Viral Vector and Gene Therapy Basics Summarized). https://biovian.com/news/viral-vector-and-gene-therapy-basics-summarized/ (Year: 2021).*
Beavers et al. miRNA Inhibition in Tissue Engineering and Regenerative Medicine. Adv Drug Deliv Rev. 88: 123-137. (Year: 2015).*
Johnson et al. Diferric transferrin regulates transferrin receptor 2 protein stability. Blood 104: 4287-4293. (Year: 2004).*
Mastroberardino et al. A novel transferrin/TfR2-mediated mitochondrial iron transport system is disrupted in Parkinson's disease. Neurobiology of Disease 34: 417-431. (Year: 2009).*
Roetto et al. The Functional Versatility of Transferrin Receptor 2 and Its Therapeutic Value. Pharmaceuticals 11: 1-20. (Year: 2018).*
Gao et al. Hepatocyte-targeted HFE and TFR2 control hepcidin expression in mice. Blood 115: 3374-3381. (Year: 2010).*
Mastroberardino, et al., "A Novel Transferrin/TfR2-Mediated Mitochondrial Iron Transport System is Disrupted in Parkinson's Disease," Neurobiology of Disease, Feb. 26, 2009, pp. 417-431, vol. 34.
International Search Report and Written Opinion in corresponding International Application No. PCT/US2023/014264, dated Jun. 22, 2023, 13 pages.

* cited by examiner

*Primary Examiner* — Kevin K Hill
*Assistant Examiner* — Keenan A Bates
(74) *Attorney, Agent, or Firm* — Fish IP Law, LLP

(57) ABSTRACT

Compositions and methods are provided that mitigate iron imbalance resulting from inflammation and/or mitigate the effects of inflammatory disease by correcting dysregulation of iron internalization. Such correction is provided by modulating expression of TFR2, transferrin, and/or hepcidin activity in an individual in need of treatment.

15 Claims, No Drawings

COMPOSITIONS AND METHODS FOR TREATING INFLAMMATORY DISEASE

The field of the invention is treatment of inflammation-related diseases and conditions.

BACKGROUND

The following description includes information that may be useful in understanding the present invention. It is not an admission that any of the information provided herein is prior art or relevant to the presently claimed invention, or that any publication specifically or implicitly referenced is prior art.

Iron is an essential nutrient that is involved in oxygen transport and acts as a cofactor in a wide range of metabolic processes and redox reactions within the cell. Iron concentration within the fluids and tissues of the body must be carefully regulated, however, as it can generate reactive oxygen species that can result in cellular damage and death. This balance between iron nutrition and toxicity is provided by systemic control mechanisms that modulate iron conservation and uptake. This is in contrast with regulation of other metals, which are controlled by eliminating simply eliminating excess. Iron and its homeostasis are closely connected with the response to inflammation and infection, and therefore are major survival mechanisms.

A large body of evidence shows that susceptibility to disease as well as response to infection and inflammation worsen with iron overload. The relationships between iron overload and infectious diseases (e.g., tuberculosis, malaria) is well documented. Iron overload resulting from hereditary hemochromatosis has been found to increase susceptibility to infectious disease. Increased susceptibility to infectious disease is also found in thalassemic patients with iron overload resulting from frequent blood transfusions. Iron status has also been found to influence the course of viral infections.

Iron status also influences the course of chronic inflammatory disease. An increase in iron stores correlates with markers of chronic inflammation in the development and progression of diabetes, obesity, and metabolic syndrome. High iron load is also involved in the development and course of neurodegenerative disease. This is significant, as not only because the prevalence of chronic diseases increasing as the population ages, but also because modified dietary iron or manipulation of iron status could represent simple preventive or therapeutic approaches.

Typically, high iron stores are reduced by phlebotomy or iron chelation therapy. While such approaches have been found to provide a degree of improvement, they do not address other effects of iron removal on necessary metabolic and energy-generating redox reactions in cells of individuals treated in this manner.

U.S. Pat. No. 9,782,453, to Nicolas et al., describes the use of hepcidin to reduce iron overload, citing observation of high tissue concentrations of iron in mice with genetic defects that reduce hepcidin expression. All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. It is not clear, however, if application of hepcidin is useful in the treatment of individuals without such a genetic defect.

United States Patent Application Publication No. 2021/0214456, to Rauner et al., describes modulating activity of transferrin receptor 2 to treat a variety of conditions. Specifically, Rauner et al. describe the use of transferrin receptor 2 inhibitors to treat anemia (such as anemia related to chronic inflammation). Use of agonists to increase transferrin receptor 2 activity, however, is limited to treatment of bone disease.

Thus, there is still a need for safe and effective methods for reducing elevated iron level in tissues of the body while avoiding negative impact to iron-related functions within the cells of an individual undergoing treatment.

SUMMARY OF THE INVENTION

The inventive subject matter provides compositions and methods for treating inflammatory disease by modulating dysregulation of iron transport into cells of an individual in need of treatment for inflammatory disease.

One embodiment of the inventive concept is a method of treating an inflammatory disease by identifying an individual in need of treatment for an inflammatory disease associated with dysregulation of iron metabolism, and modifying one or more cell(s) of the individual to up-regulate expression of Transferrin Receptor 2 (TFR2). Examples of such diseases include Parkinson Disease, Alzheimer's disease, a viral disease (e.g., infection with a coronavirus such as SARS-CoV-2), and inflammatory response to a pathogen. The TFR2 can include alpha Transferrin Receptor 2 (αTFR2) and/or beta Transferrin Receptor 2 (βTFR2). In some embodiments the method includes introducing an expression vector that encodes at least one of αTFR2 and βTFR2. In other embodiments the method includes introducing an expression vector that encodes a factor that interacts with a regulatory element associated with at least one of αTFR2 and βTFR2. In such methods the expression vector can be a virus, such as a genetically modified influenza virus or adenovirus, and can include an inducible promoter. In some embodiments the method can also include a supplemental iron removal therapy, such as phlebotomy and chelation therapy.

Another embodiment of the inventive concept is a composition or formulation for treating an inflammatory disease that includes an expression vector that includes a gene sequence that upregulates expression of TFR2. The TFR2 can include alpha Transferrin Receptor 2 (αTFR2) and/or beta Transferrin Receptor 2 (βTFR2). In some embodiments the expression vector includes a region encoding TFR2. In other embodiments the expression vector encodes a factor that interacts with a regulatory element associated with TFR2 (e.g., at least one of αTFR2 and βTFR2). The expression vector can provide within a virus, such as a genetically modified influenza virus or adenovirus, and can include a promoter. In other embodiments the expression vector can be provided within a micelle or liposome.

Another embodiment of the inventive concept is a method of treating or preventing dysregulation of iron storage or metabolism in an individual by determining that the individual has a genetic predisposition towards a disorder of iron storage or metabolism, then modifying a cell of the individual to up-regulate expression of TFR2. The TFR2 can include alpha Transferrin Receptor 2 (αTFR2) and/or beta Transferrin Receptor 2 (βTFR2). In some embodiments the cell can be modified by introducing an expression vector that encodes at least one of αTFR2 and βTFR2 into the cell. In other embodiments the cell can be modified by introducing an expression vector that encodes a factor that interacts with a regulatory element associated with at least one of αTFR2 and βTFR2. In some embodiments the expression vector can be provided by a virus, such as a genetically modified influenza virus or adenovirus. In other embodiments the expression vector can be provided within a micelle or liposome. In some embodiments the expression vector encodes an inducible promoter.

Various objects, features, aspects and advantages of the inventive subject matter will become more apparent from the following detailed description of preferred embodiments.

DETAILED DESCRIPTION

The presence of high circulating concentration of iron (i.e., in the form of ferritin) is frequently associated with inflammatory processes. Typically, this is treated using therapies that deplete the body's iron stores (e.g., phlebotomy) or that complex circulating iron (e.g., chelation therapy). The Inventor contemplates an alternative approach, in which high circulating concentrations of iron associated with inflammatory processes are a result of dysregulation of internalization of iron by cells of the body, which can result in elevated concentrations of circulating iron and dysfunction of iron-related processes (e.g., mitochondrial production of ATP) within cells of the body due to inadequate iron within the cells. This can be addressed by increasing cellular iron internalization, for example by upregulating expression or otherwise increasing the content of proteins of the cell that are involved in iron internalization. Such proteins include, but are not limited to, transferrin receptor 2 (TFR2) and forms thereof (e.g., αTFR2, βTFR2). As a result, circulating iron concentrations are reduced and iron-related metabolic processes in cells of the body are corrected.

One should appreciate that the reduction in circulating iron concentrations coupled with increased cellular internalization of iron, with a concomitant reduction in inflammation or at least some of the deleterious effects of inflammation can reduce symptoms and improving outcome in a wide variety and inflammatory and inflammation-related diseases and conditions.

The following discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The Inventor believes that the association between serum iron concentration and inflammation (and diseases and/or conditions resulting from such inflammation) can be understood, at least in part, as a dysregulation of iron transport into cells of the human body. For example, excessive circulating iron (e.g., ferritin in the bloodstream) can result in impaired transport of iron into tissues and/or cells of the body. Specifically, such effects can result in insufficient transport of iron into cells, which in turn negatively impacts mitochondrial function. Iron is utilized as a cofactor in mitochondrial processes that provide ATP and other molecules necessary for normal cell function. The Inventor believes that elevated serum iron concentrations (for example, as a result of an inflammatory condition) can cause or at least in part result from of a dysregulation or impairment of iron transport into the cells. Such dysregulation can result in or be a result of elevated iron concentration in serum, which can in turn lead to sub-optimal iron concentration within the cells (e.g., due to dysregulated, which can impair mitochondrial function. This impairment of mitochondrial function impairs cell function, resulting in the development or exacerbation of disease in the individual. Such exacerbation can contribute to the effects of inflammatory disease.

Accordingly, correction or even partial correction of such dysregulation of iron transport into the cell can act to cure or at least partially alleviate diseases and conditions associated with inflammation related to dysregulation of iron transport. Similarly, correction or even partial correction of such dysregulation of iron transport into the cell can act to restore more normal cellular function and mitigate the effects of an inflammatory condition and/or improve the effects of conventional treatment for an inflammatory condition. Such correction can be achieved, for example, by increasing iron transport into the cells.

One embodiment of the inventive concept is a method of treating or mitigating the effects of an inflammatory disease by modifying cells of an individual with or at risk of the inflammatory disease to increase their uptake of iron. Examples of inflammatory disease that can be treated include, but are not limited to, Alzheimer's disease, Parkinson disease, Behcet's disease, neurodegenerative disease, heart disease, diabetes, cancer, arthritis, ankylosing spondylitis, asthma, type 2 diabetes, an inflammatory response to infection (e.g., viral, bacterial, fungal, or protozoan infection), and infection with a coronavirus (e.g., SARS-CoV-2).

In some embodiments correction of the dysregulation of iron transport into cells can be utilized to mitigate damage to tissues and/or cells of the body resulting from inflammatory diseases or processes. For example, damage to tissues and/or cells of the body can be reduced or eliminated as underlying and treatable causes of inflammation are addressed. Examples of such underlying and treatable causes of inflammation include poor diet, vitamin deficiency, obesity, stress, and infection.

An initial step in such a method can be identifying an individual that has or is at risk of developing such an inflammatory disease. This can be accomplished by any suitable means. For example, such an individual can be identified on the basis of current symptoms, medical history, and/or laboratory results indicative of dysregulation of iron concentration and/or the inflammatory disease. In some embodiments such an individual can be identified on the basis of their genetics and/or family history. For example, an individual can be identified as having or being at risk of developing such an inflammatory disease based on DNA sequencing, characterization of their RNA expression, characterization of their proteome, genetic analysis of relatives, and/or a family history of the inflammatory disease and/or dysregulation of iron concentration. In some embodiments the individual in need of treatment is symptomatic. In other embodiments the individual in need of treatment is asymptomatic. In some embodiments of the inventive subject matter the individual in need of treatment shows a genetic predisposition towards development of an inflammatory disease related to iron dysregulation (e.g., by family history, genetic studies, etc.) but shows no indication of having yet developed the disease. In such individual's treatment can be considered prophylactic.

In some embodiments an individual in need of treatment can be identified by characterizing efficiency in internalization of circulating iron into their tissues. For example, circulating iron concentration can be characterized by measuring the concentration of circulating ferritin, whereas tissue and/or cellular uptake of iron can be characterized by measuring iron content of a tissue sample obtained from the patient. Significant deviation from mean or median values derived from a normal or healthy population (e.g., a 5%, 10%, 15%, 20%, 25%, 35%, 50%, 75%, 90%, or more reduction in a tissue or cellular iron content to circulating iron content ratio) can be considered indicative of impaired iron internalization. Alternatively, tissue or cellular iron content can be similarly comparted to those of normal or healthy individuals to determine if overall iron internalization is abnormal.

On identifying an individual in need of treatment for an inflammatory disease associated with dysregulation of iron metabolism and/or iron dysregulation as a result of inflammation, the individual can be treated to increase cellular iron uptake. In some embodiments this can be accomplished by modifying a cell of the individual to up-regulate expression of Transferrin Receptor 2 (TFR2). It should be appreciated that TFR2 occurs in different forms, and that such up-regulation can be directed to alpha Transferrin Receptor 2 (αTFR2), beta Transferrin Receptor 2 (βTFR2), or both.

Up-regulation of TFR2 within cells of the individual to be treated can be accomplished by any suitable means. In some embodiments such up-regulation can be accomplished by introducing an expression vector that encodes αTFR2, βTFR2, or both αTFR2 and βTFR2 into cells. Alternatively, such up-regulation can be accomplished by introducing an expression vector that encodes a factor that interacts with a regulatory element located upstream from an endogenous or native gene encoding αTFR2, βTFR2, or both αTFR2 and βTFR2, where such interaction results in increased expression of the endogenous or native gene. The resulting increase in TFR2 content in the modified cell can act to increase transport of iron from the surrounding environment into the cell, thereby improving or restoring mitochondrial function while decreasing serum iron concentrations.

Such an expression vector can take any suitable form. In some embodiments the expression vector is a genetically modified virus. Suitable viruses include retroviruses, herpes viruses, pox viruses, influenza viruses, and adenoviruses. Such viruses can be modified, for example by genetic modification and/or attenuation, to reduce virulence. For example, virulence of a pox virus utilized as a vector of the inventive concept can be reduced by attenuation through repeated passage through non-host species cells in culture. In some embodiments a viral vector can be used that is known to be rapidly cleared by the immune system. In other embodiments a viral vector can be used that produces a persistent infection or that modifies DNA of the host cell in order to provide a persistent effect.

Alternatively, in some embodiments an expression vector can be provided in a micelle, liposome, or similar synthetic membrane package. Such a micelle or liposome can incorporate proteins, sugars, or other biomolecules into the exposed surface in order to facilitate targeting of and/or incorporation of cells of the individual being treated. For example, such a micelle or lipid can enclose a nucleic acid encoding for TFR2 and/or a factor that upregulates endogenous TFR2 expression and carry receptors for cell surface markers characteristic of target cells within the individual to be treated.

In some embodiments the expression vector can include a promoter positioned upstream of an encoding region that encodes for αTFR2, βTFR2, both αTFR2 and βTFR2, or a regulatory factor that increases expression of endogenous αTFR2 and/or βTFR2. Such a promoter can be a promoter that is normally present in the vector being used, for example a promoter that is present in the wild-type viral genome prior to genetic modification. Alternatively, such a promoter can be introduced through genetic engineering techniques as are known in the art. In such embodiments the promoter can be inducible, thereby providing control of when the encoding region is transcribed. In such embodiments administration of the vector to the individual to be treated can be accompanied by or followed with administration of a compound that interacts with the promoter, thereby inducing transcription of the encoding region at a desired time point and/or for a desired duration.

Alternatively, TFR2 (e.g., αTFR2, βTFR2, or both αTFR2 and βTFR2) or active fragments thereof can be provided to cells as functional proteins, functional peptides, or precursors that are processed by the cell into active forms. For example, such proteins, peptides, or precursors can be provided within a micelle or liposome that can fuse with or be internalized by cells of the individual to be treated. Such a micelle or liposome can incorporate proteins, sugars, or other biomolecules into the exposed surface in order to facilitate targeting of and/or incorporation of cells of the individual being treated. For example, such a micelle or lipid can enclose TFR2, a functional fragment of TFR2, and/or a precursor of TFR2 and carry receptors for cell surface markers characteristic of target cells within the individual to be treated.

Transferrin is a glycoproteins that is produced in the liver and binds iron, mediating its transport in blood. Each molecule of transferrin contains binding sites for two $Fe^{3+}$ ions; binding to transferrin renders these ions nontoxic. Transferrin binds iron tightly but reversibly, releasing the bound iron at the low pH encountered following complexation with transferrin receptor and subsequent transport into the cell.

In some embodiments methods of the inventive concept can include modulating transferrin content of the blood plasma in an individual in need of treatment for dysregulation of iron transport, such as those causing or resulting from inflammation. In some embodiments exogenous transferrin protein can be provided to the individual, for example by injection or infusion into the bloodstream. In such embodiments transferrin can be modified to increase serum half-life, for example by PEGylation.

In other embodiments expression of transferrin in an individual being treated can be upregulated, thereby causing an increase in the release of transferrin into the bloodstream. Up-regulation of transferrin expression in the individual to be treated can be accomplished by any suitable means. In some embodiments such up-regulation can be accomplished by introducing an expression vector that encodes transferrin into cells of the individual being treated. Alternatively, such up-regulation can be accomplished by introducing an expression vector that encodes a factor that interacts with a regulatory element located upstream from an endogenous or native gene encoding transferrin, where such interaction results in increased expression of the endogenous or native gene. The resulting increase in transferrin content in individual's bloodstream can act to increase transport into the cell, thereby improving or restoring mitochondrial function while decreasing serum iron concentrations.

Such an expression vector can take any suitable form. In some embodiments the expression vector is a genetically modified virus. Suitable viruses include retroviruses, herpes viruses, pox viruses, influenza viruses, and adenoviruses. Such viruses can be modified, for example by genetic modification and/or attenuation, to reduce virulence. For example, virulence of a pox virus utilized as a vector of the inventive concept can be reduced by attenuation through repeated passage through non-host species cells in culture. In some embodiments a viral vector can be used that is known to be rapidly cleared by the immune system. In other embodiments a viral vector can be used that produces a persistent infection or that modifies DNA of the host cell in order to provide a persistent effect.

Alternatively, in some embodiments an expression vector can be provided in a micelle, liposome, or similar synthetic membrane package. Such a micelle or liposome can incorporate proteins, sugars, or other biomolecules into the exposed surface in order to facilitate targeting of and/or incorporation of cells of the individual being treated, with subsequent release of transferrin into circulation. For example, such a micelle or lipid can enclose a nucleic acid encoding for transferrin and/or a factor that upregulates endogenous transferrin expression and carry receptors for cell surface markers characteristic of target cells within the individual to be treated.

In some embodiments the expression vector can include a promoter positioned upstream of an encoding region that encodes for transferrin, or a regulatory factor that increases expression of endogenous transferrin. Such a promoter can be a promoter that is normally present in the vector being used, for example a promoter that is present in the wild-type viral genome prior to genetic modification. Alternatively, such a promoter can be introduced through genetic engineering techniques as are known in the art. In such embodiments the promoter can be inducible, thereby providing control of when the encoding region is transcribed. In such embodiments administration of the vector to the individual to be treated can be accompanied by or followed with administration of a compound that interacts with the promoter, thereby inducing transcription of the encoding region at a desired time point and/or for a desired duration.

In some embodiments methods to increase transferrin content in an individual's bloodstream can be combined, for example combining administration of transferrin via injection or infusion with administration of an expression vector encoding transferrin. In some embodiments methods to increase transferrin content in an individual can be combined with methods to increase TFR2 content or expression in cells of an individual being treated, as described above. The Applicant believes that such an increase in transferrin content in blood plasma in combination with an increase in TFR2 content of cells can provide a synergistic (i.e., greater than additive effect) in correcting dysregulation of iron transport into cells, in particular cells of an individual with an inflammatory condition.

Hepcidin is another regulator of iron metabolism, and acts by binding to the iron export channel ferroport and inhibiting its function. Such inhibition can result in iron sequestration within cells. In some embodiments of the inventive concept dysregulation of iron transport as a result of inflammation and/or inflammation resulting from dysregulation of iron transport can be at least partially corrected by increasing hepcidin expression. This can be accomplished by modifying a cell of the individual to up-regulate expression of hepcidin.

Up-regulation of hepcidin within cells of the individual to be treated can be accomplished by any suitable means. In some embodiments such up-regulation can be accomplished by introducing an expression vector that encodes hepcidin into cells. Alternatively, such up-regulation can be accomplished by introducing an expression vector that encodes a factor that interacts with a regulatory element located upstream from an endogenous or native gene encoding hepcidin, where such interaction results in increased expression of the endogenous or native gene. The resulting increase in hepcidin content in the modified cell can act to decrease loss of iron from the cell, thereby improving or restoring mitochondrial function while decreasing serum iron concentrations.

Such an expression vector can take any suitable form. In some embodiments the expression vector is a genetically modified virus. Suitable viruses include retroviruses, herpes viruses, pox viruses, influenza viruses, and adenoviruses. Such viruses can be modified, for example by genetic modification and/or attenuation, to reduce virulence. For example, virulence of a pox virus utilized as a vector of the inventive concept can be reduced by attenuation through repeated passage through non-host species cells in culture. In some embodiments a viral vector can be used that is known to be rapidly cleared by the immune system. In other embodiments a viral vector can be used that produces a persistent infection or that modifies DNA of the host cell in order to provide a persistent effect.

Alternatively, in some embodiments an expression vector can be provided in a micelle, liposome, or similar synthetic membrane package. Such a micelle or liposome can incorporate proteins, sugars, or other biomolecules into the exposed surface in order to facilitate targeting of and/or incorporation of cells of the individual being treated. For example, such a micelle or lipid can enclose a nucleic acid encoding for hepcidin and/or a factor that upregulates endogenous hepcidin expression and carry receptors for cell surface markers characteristic of target cells within the individual to be treated.

In some embodiments the expression vector can include a promoter positioned upstream of an encoding region that encodes for hepcidin, or a regulatory factor that increases expression of endogenous hepcidin. Such a promoter can be a promoter that is normally present in the vector being used, for example a promoter that is present in the wild-type viral genome prior to genetic modification. Alternatively, such a promoter can be introduced through genetic engineering techniques as are known in the art. In such embodiments the promoter can be inducible, thereby providing control of when the encoding region is transcribed. In such embodiments administration of the vector to the individual to be treated can be accompanied by or followed with administration of a compound that interacts with the promoter, thereby inducing transcription of the encoding region at a desired time point and/or for a desired duration.

Alternatively, hepcidin or active fragments thereof can be provided to cells as functional proteins, functional peptides, or precursors that are processed by the cell into active forms. For example, such proteins, peptides, or precursors can be provided within a micelle or liposome that can fuse with or be internalized by cells of the individual to be treated. Such a micelle or liposome can incorporate proteins, sugars, or other biomolecules into the exposed surface in order to facilitate targeting of and/or incorporation of cells of the individual being treated. For example, such a micelle or lipid can enclose hepcidin, a functional fragment of hepcidin, and/or a precursor of hepcidin and carry receptors for cell surface markers characteristic of target cells within the individual to be treated.

In some embodiments methods to increase hepcidin content in an individual's cells can be combined with methods to increase TFR2 content or expression in cells of an individual being treated and/or increasing transferrin content in the individual's bloodstream, as described above. The Applicant believes that such an increase in cellular hepcidin content in combination with an increase in TFR2 content of cells and/or transferrin content in blood plasma can provide a synergistic (i.e., greater than additive effect) in correcting dysregulation of iron transport into cells, in particular cells of an individual with an inflammatory condition.

In some embodiments, methods of the inventive concept can also incorporate one or more supplemental iron removal or complexation therapy(ies) in a treatment plan for an individual to be treated. Such a supplemental iron removal therapy can be provided prior to, during, or after administration of compositions as described above. Suitable supplemental iron removal or complexation therapies include phlebotomy and/or chelation therapy. The Inventor believes that synergistic (i.e., greater than additive) effects are observed in regard to reduction in symptoms and/or improvement in disease state on combined use of the compositions described above and a supplemental iron removal or complexation therapy.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A method of treating an inflammatory disease or iron transport dysregulation resulting from inflammation, comprising:
   identifying an individual in need of treatment for an inflammatory disease associated with dysregulation of iron metabolism or iron transport dysregulation resulting from inflammation; and
   modifying a cell in the individual to up-regulate expression of Transferrin Receptor 2 (TFR2), wherein modifying the cell comprises introducing an expression vector that encodes at least one of alpha Transferrin Receptor 2 (αTFR2) and beta Transferrin Receptor 2(βTFR2).

2. The method of claim 1, wherein modifying the cell comprises introducing a virus comprising an expression vector.

3. The method of claim 2, wherein the virus is a genetically modified influenza virus or adenovirus.

4. The method of claim 1, wherein modifying the cell comprises introducing an expression vector that comprises an inducible promoter.

5. The method of claim 1, wherein the inflammatory disease is selected from the group consisting of Parkinson Disease, Alzheimer's disease, a viral disease, and inflammatory response to a pathogen.

6. The method of claim 1, further comprising providing a supplemental iron removal therapy to the individual.

7. The method of claim 6, wherein the supplemental iron removal therapy is selected from the group consisting of phlebotomy and chelation therapy.

8. A composition for treating an inflammatory disease or dysregulation of iron transport resulting from inflammation, comprising an expression vector comprising a gene sequence that upregulates expression of TFR2, wherein the expression vector encodes at least one of αTFR2 and βTFR2.

9. The composition of claim 8, wherein the expression vector is a virus.

10. The composition of claim 9, wherein the virus is a genetically modified influenza virus or adenovirus.

11. The composition of claim 8, wherein the expression vector comprises an inducible promoter.

12. A method of treating or preventing dysregulation of iron storage or metabolism in an individual, comprising:
   determining that the individual has a genetic predisposition towards a disorder of iron storage or metabolism; and
   modifying a cell of the individual to up-regulate expression of TFR2, wherein modifying the cell comprises introducing an expression vector that encodes at least one of αTFR2 and βTFR2.

13. The method of claim 12, wherein modifying the cell comprises introducing a virus comprising an expression vector.

14. The method of claim 13, wherein the virus is a genetically modified influenza virus or adenovirus.

15. The method of claim 12, wherein modifying the cell comprises introducing an expression vector that comprises an inducible promoter.

\* \* \* \* \*